United States Patent [19]

Portner et al.

[11] 4,126,132
[45] Nov. 21, 1978

[54] INTRAVENOUS AND INTRA ARTERIAL DELIVERY SYSTEM

[75] Inventors: Peer M. Portner, Berkeley; Jal S. Jassawalla, San Francisco, both of Calif.

[73] Assignee: Andros Incorporated, Berkeley, Calif.

[21] Appl. No.: 701,238

[22] Filed: Jun. 30, 1976

Related U.S. Application Data

[63] Continuation-in-part of Ser. No. 599,330, Jul. 28, 1975, abandoned.

[51] Int. Cl.² .............................................. A61M 5/00
[52] U.S. Cl. ........................ 128/214 F; 128/DIG. 12; 128/273; 417/454; 417/468
[58] Field of Search ........... 128/214 R, 214 E, 214 F, 128/214.2, DIG. 12, DIG. 13, 273; 417/459, 465, 468, 454

[56] References Cited

U.S. PATENT DOCUMENTS

| | | | |
|---|---|---|---|
| 3,039,399 | 6/1962 | Everett | 128/DIG. 3 |
| 3,496,878 | 2/1970 | Hargest et al. | 128/214 F |
| 3,620,650 | 11/1971 | Shaw | 417/476 X |
| 3,874,826 | 4/1975 | Lundquist | 128/214 F X |
| 3,901,231 | 8/1975 | Olson | 128/214 F |
| 3,976,402 | 8/1976 | Lundquist | 128/214 E X |
| 3,985,133 | 10/1976 | Jenkins et al. | 128/214 F |
| 3,993,061 | 11/1976 | O'Leary | 128/214 F |

Primary Examiner—Dalton L. Truluck
Attorney, Agent, or Firm—Fitch, Even, Tabin & Luedeka

[57] ABSTRACT

An intravenous and intra arterial delivery system is described having a disposable cassette actuated by a pump and control electronics for providing positive but variable delivery rates. The cassette is self-priming and provides protection against the delivery of air by being unable to impel air, and means provide an indication of excessive air in the cassette. The electronics has low power consumption so as to be suitable for battery operation, such as by way of rechargeable batteries. A pressure sensor in the delivery line may be used to sense infiltration. The system further features a provision for predetermining the amount of fluid to be delivered, and a detection system for detecting an empty supply bottle.

11 Claims, 16 Drawing Figures

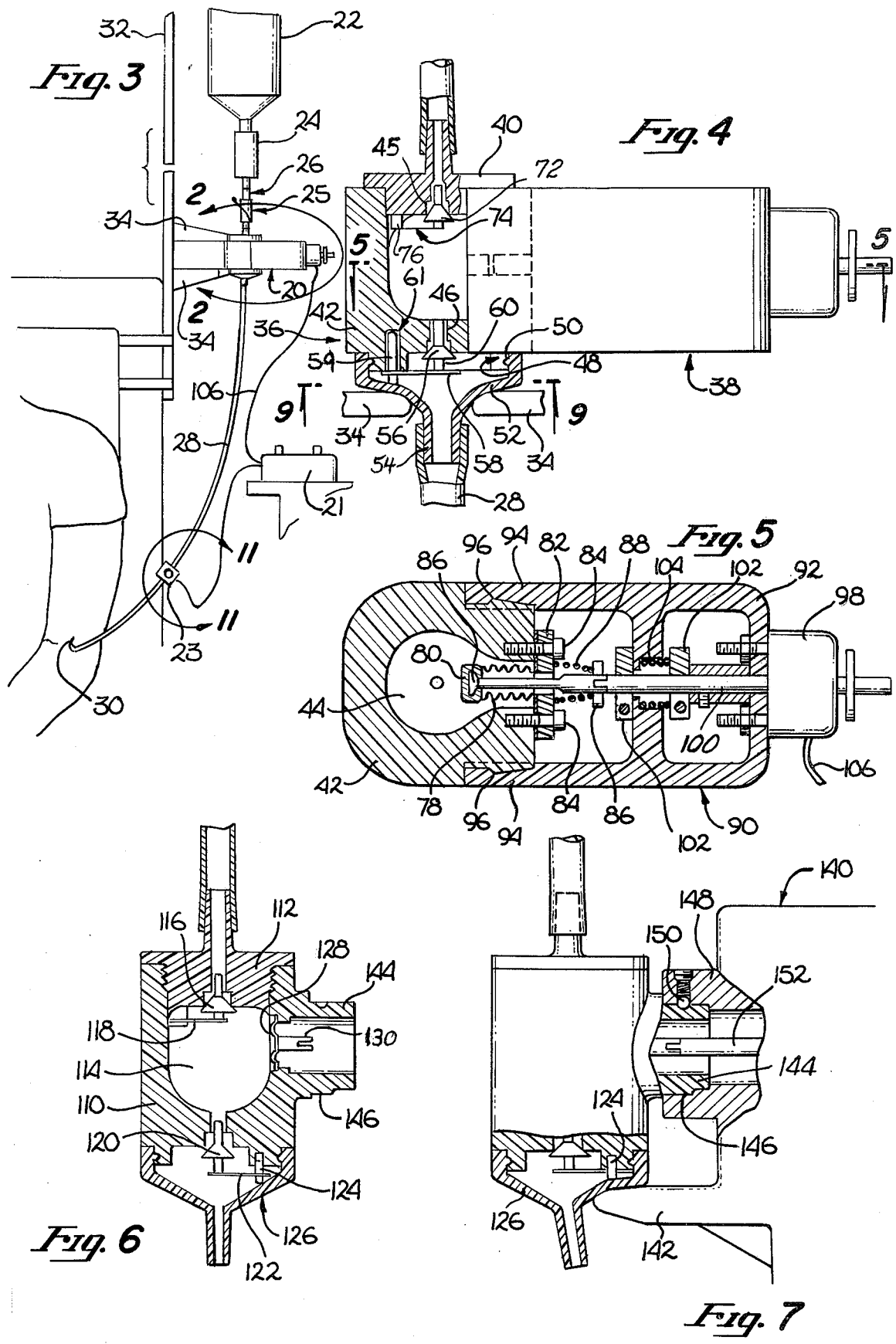

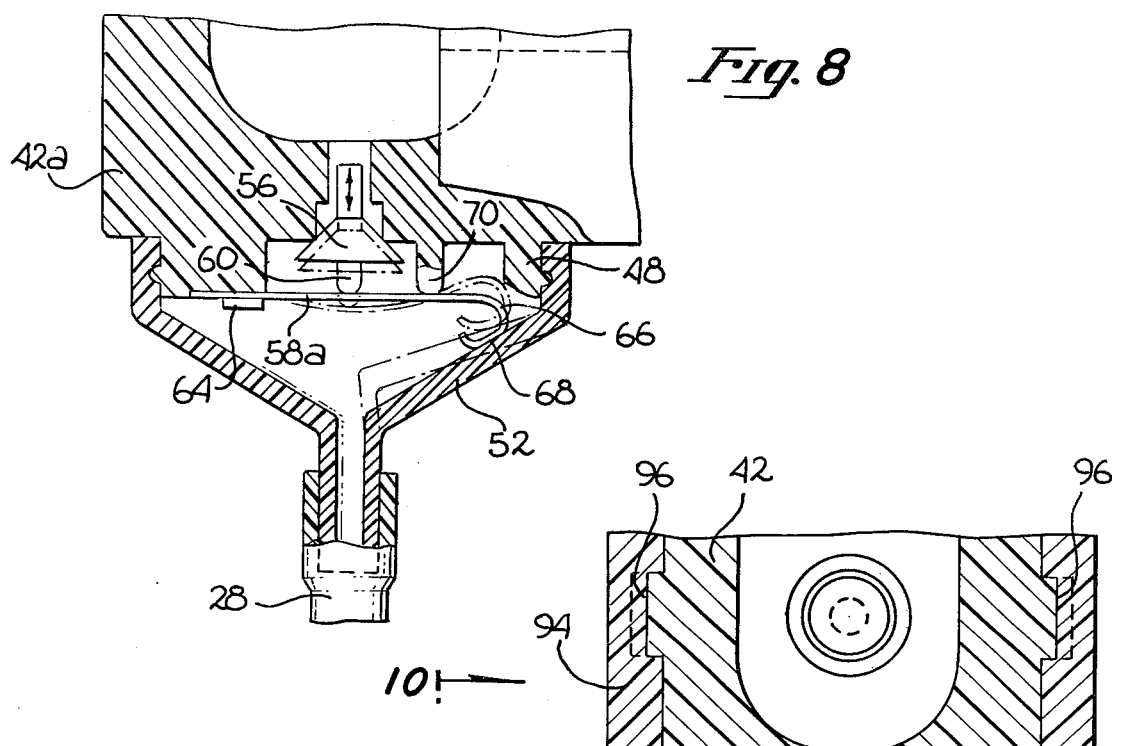
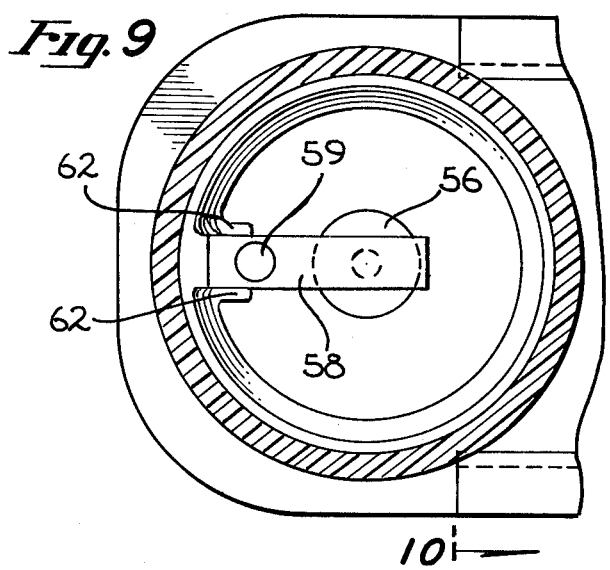
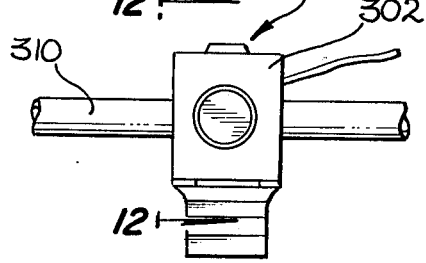
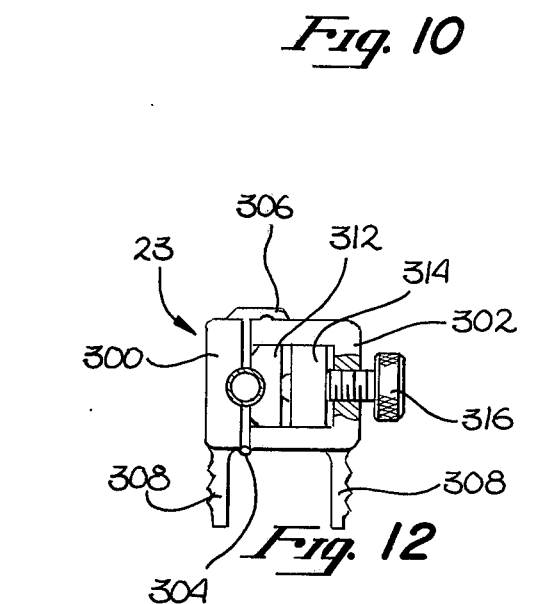

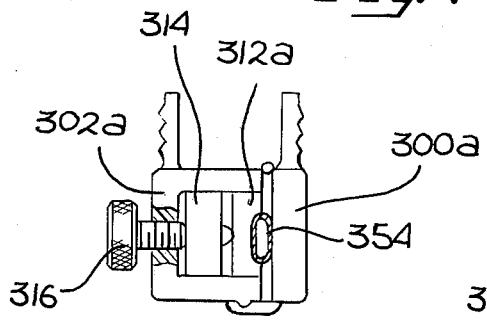
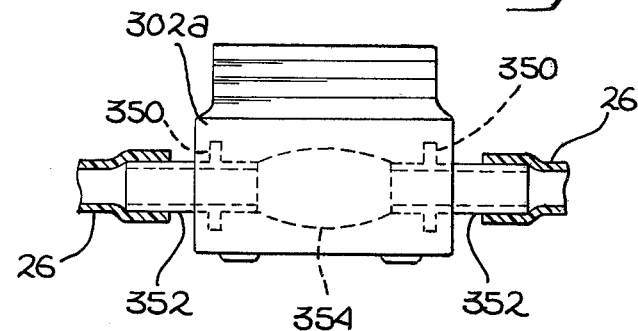
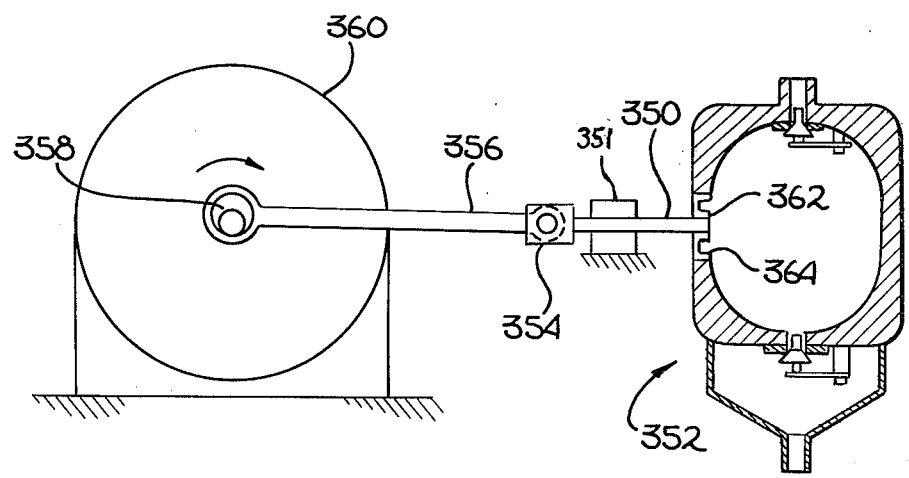

INTRAVENOUS AND INTRA ARTERIAL DELIVERY SYSTEM

This invention is a continuation-in-part of U.S. Application Ser. No. 599,330, filed July 28, 1975 and now abandoned.

The present invention relates to the field of medical fluid delivery systems and, more particularly, to intravenous delivery systems for the delivery of drugs, plasma, glucose solutions and the like.

Various systems for the delivery of fluids intravenously or intra arterially are well known in the prior art, and such systems are in widespread daily use in hospitals throughout the world. These systems (I. V. systems) are commonly used for the intravenous or intra arterial delivery of such fluids as glucose solutions and blood plasma, and for the delivery of drugs, all at controlled delivery rates depending on the patient's needs, and in the case of drugs, the drug concentration being delivered.

The oldest and most commonly used form of delivery system is comprised of a fluid container, a drip chamber and an adjustable clamp in the tube leading from the drip chamber to the needle penetrating the vein. The fluid container or bottle is supported at an elevated position with respect to the patient, with the drip chamber typically immediately thereunder. Transparent walls in the drip chamber coupled with a fixed volume of air therein allows the visual determination of the drip rate, which in turn is adjustable by the hose clamp. Thus, as fluid being delivered seeps past the pinched area of the hose, the air pressure in the drip chamber decreases, thereby encouraging the formation and dislodging of a drop from the tip of the small tube into the drip chamber coupled to the bottle. Such systems may be used alone, or the drip chamber used in conjunction with some other type of metering or pumping mechanism so that the visually observed drip rate may be used as a cross-check to verify the proper operation of the pumping device.

Another type of I.V. system which has come into substantial use in recent years utilizes what is commonly referred to as some form of a peristaltic pump. Such pumps are characterized by a length of flexible tubing which is disposed within an arc between a stator-like member and a rotor assembly. The rotor assembly is provided with a plurality of rollers which, upon rotation of the rotor assembly, successively pinch-off the tube and advance the location of the pinch-off so as to progressively advance the fluid within the tube along the tube at a rate determined by the rate of rotation of the rotor. Typically such systems are driven in rotation by some form of motor-gear assembly so as to provide the generally desired low pumping rate by the low speed rotation of the rotor. Such pumps have the advantage of having a disposable element in the fluid flow path, in that the length of tubing in the pump may be replaced after each use. In principle, the pumps also have the further advantage of providing the low and variable flow rates by way of a positive displacement pump. In practice, however, these systems characteristically exhibit poor accuracy and poor reproducibility. They also have the disadvantages of being able to pump air, and both air and liquid continuously against a rather substantial back pressure. They are mechanically complex, and require a substantial amount of power, thereby making them relatively expensive and difficult to use on battery operation.

Another form of pump is the positive displacement pump of U.S. Pat. No. 3,620,650. The pumps disclosed therein have some advantages over the previously described pumps in that they are specifically configured so as to not pump air, thereby providing for automatic shut-off of the pump in the event of exhaustion of the supply of fluid being injected. Also, the pump utilizes a form of electromagnetic device allowing a pulse source to provide a variable pulse rate to thereby vary the pump rate. The pump disclosed therein, howwever, has a number of disadvantages in comparison to the present invention. In particular, the pump of FIG. 4 of U.S. Pat. No. 3,620,650 is a relatively expensive pump which must be fabricated from a relatively large number of close tolerance parts. Aside from coil springs and a close fitting piston therein, the pump requires a magnetic member within the fluid chamber which in itself has certain disadvantages. Obviously, the magnetic member must be a metal member and accordingly, must be suitably protected against corrosion, etching, and other adverse effects thereon which may be caused by any of the wide range of fluids which might be injected. Even if it is used as a disposable pump so that deterioration of the pump would not be cumulative, all deterioration of pump parts must be avoided because of possible adverse effects of any dissolved materials. Also, since the magnetic member is within the fluid chamber whereas the actuating coil is external to the enclosure, considerable electrical power is required to actuate the solenoid, thereby making battery operation very difficult.

Another positive displacement pump is that shown in U.S. Pat. No. 3,874,826. This pump is also relatively mechanically complex, and like the pump of U.S. Pat. No. 3,620,650, not ideally suited for disposable use because of its complexity and apparent high cost. For example, because the pump employs a piston protruding a substantial distance into the pumping chamber, a germ barrier sleeve must be employed. Severe problems of fit and friction induced wear inherently result from such a construction.

It is an object of the present invention to provide an improved pumping system for use in an intravenous delivery system.

Another object of the invention is to provide a low cost disposable cassette for use in an intravenous delivery system and which connects with a pump therein.

A further object of the invention is to provide an intravenous delivery system having improved operational characteristics over the prior art and which is relatively low in cost and of high reliability.

Other objects of the invention will become apparent to those skilled in the art from the following description, taken in connection with the accompanying drawings wherein:

FIG. 3 is a view of an intravenous delivery system illustrating how one embodiment of the present invention may be employed;

FIG. 4 is a partial cross section of the pumping system of FIG. 3;

FIG. 5 is a partial cross section of the embodiment of FIG. 3;

FIG. 6 is a partial cross section of still another embodiment cassette;

FIG. 7 is a further partial cross section of the embodiment of FIG. 6;

FIG. 8 is a partial cross section of a cassette similar to that of FIG. 4 showing an alternate form of outlet valve taken on an expanded scale;

FIG. 9 is a cross section taken along line 9—9 of FIG. 4;

FIG. 10 is a partial cross section taken along lines 10—10 of FIG. 9;

FIG. 11 is a side view of an infusion pressure sensor;

FIG. 12 is an end view of the pressure sensor of FIG. 11 taken along line 12—12 of FIG. 11;

FIG. 14 is a partial cross section of an alternate embodiment pressure sensor;

FIG. 15 is a side view of the alternate embodiment pressure sensor of FIG. 14 illustrating certain aspects of the internal construction thereof; and FIG. 16 is a schematic representation of an alternate embodiment wherein the pump employs a stepper motor.

Very generally, the pumping system of the invention, which is employed in an intravenous delivery system, comprises a pump and a disposable cassette adapted to be detachably secured to the pump. The pump includes a driver element adapted for reciprocatory motion through a predetermined stroke distance upon energization of the pump. The cassette has wall means defining a pumping chamber with inlet and outlet ports adapted for series connection in the flow of fluid in the intravenous delivery system. The wall means which define the chamber of the cassette include deformable portions for varying the volume of the chamber. The drive element of the pump is positioned to engage the deformable portion of the wall means with the cassette secured to the pump throughout movement of the driver element through the predetermined stroke distance.

Figures 1, 2:
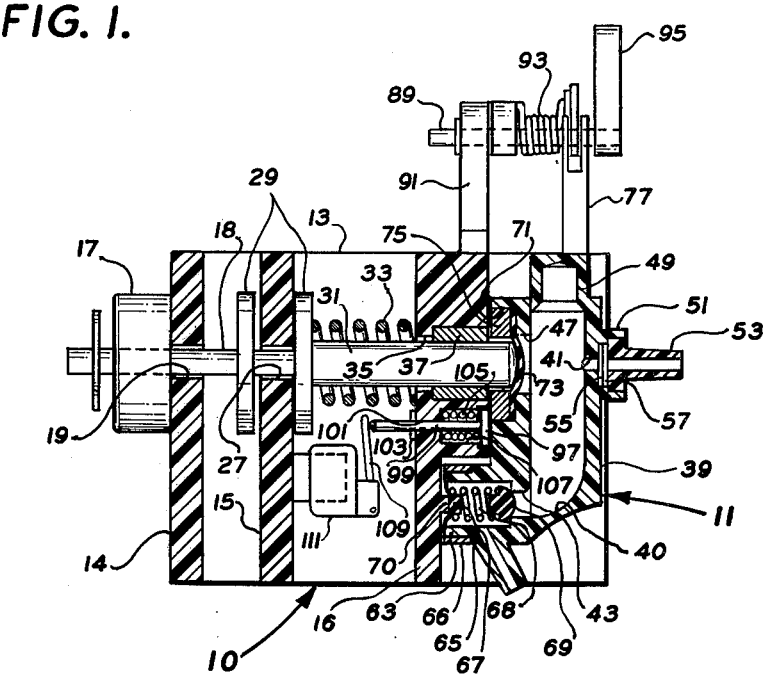
FIG. 1 is a full section side view of a pumping system constructed in accordance with the invention.
FIG. 2 is a front elevational view of the system of FIG. 1.

Referring now more particularly to FIGS. 1 and 2, a preferred form of the system of the invention is shown. The form of the invention illustrated in FIGS. 1 and 2 is intended for use as a unit contained in a housing, not shown, to be disposed on a table adjacent the bedside of the patient receiving the intravenous or intra arterial fluid. The unillustrated housing contains suitable controlling electronics, such as those described in connection with FIG. 13 below, and also serves to support the pump 10 and cassette 11 which, together with the electronics, comprise the pumping system of the invention.

The pump 10, which is mounted in the unillustrated housing described above, includes a pump support structure comprising a pair of side walls 13 and three transverse walls 14, 15, and 16, extending perpendicularly of the side walls and spaced from each other. A solenoid actuator 17 is mounted to the wall 14 and has a movable actuator member 18 extending through an opening 19 in the wall 14 and through a further opening 27 in the wall 15. Two limit stop members 29 are mounted on the rod 18 on opposite sides of the wall 15 to limit the axial motion of the rod 18 moved by the solenoid actuator 17.

A pump driver element 31 is secured to the end of the rod 18 opposite the solenoid actuator 17. A coil spring 33 surrounds the driver element 31 and extends from the wall 16 to abut the nearest one of the stop members 29. This serves to bias the driver element to the left as viewed in FIG. 1. The driver element extends through an opening 35 in the wall 16, being supported by a suitable bearing 37.

The cassette 11 includes a body member 39 which is preferably an injection molded plastic material. The body member is formed to have an internal chamber or cavity 40, preferably rounded or chamfered so as to be free of corners. Three openings are provided in the body member 39 to provide access to the cavity 40. These openings include an inlet opening 41, an outlet opening 43, and a membrane opening 47. The body member 39 is also shaped at its uppermost surface to form a bulb or cap 49 for reasons which will be described in detail below.

An annular lip 51 is formed in the outer surface of the body member 39 surrounding the inlet opening 41. A nipple 53 is seated in the space defined by the annular lip 51 and is positioned against a step to leave a valve chamber 55. A disc 57 positioned within the valve chamber 55 is so designed as to provide a check valve to prevent flow out of the inlet opening 41 and to allow flow only through the inlet opening 41 into the chamber or cavity 40. The nipple 53 is adapted for connection to a solution bottle, either through tubing or through a suitable bottle connector. Inasmuch as the invention performs a pumping function, it is typically unnecessary to elevate the solution bottle to the extent required in more conventional IV delivery systems.

An annular lip 63 is formed in the body member 39 surrounding the outlet opening 43. A nipple 64 communicates from the interior of the annular lip 63 to a position below the cassette and is adapted for connection to a tube leading to a catheter or needle inserted in the patient. A membrane 65 closes the chamber formed by the annular lip 63 and is held in place by an annular clamping ring 66. The membrane 65 is provided with a central plug 67 which supports a coil spring 68 which extends axially from the membrane 65 toward the outlet opening 43. The coil spring supports a mushroom-shaped valve 69 which seats in the opening 43. The force of the spring 68 is normally insufficient to bias the valve 69 to close the opening 43. However, with the cassette mounted to the pump as shown, the force is sufficient to bias the valve to the closed position when the membrane 65 is engaged by a stop 70 on the wall 16.

An annular recess 71 is provided in the outer surface of the body member 39 surrounding the opening 47. An impermeable resilient membrane 73 extends across the opening and is retained with its periphery in the recess 71 by means of an annular retainer 75. As may be seen from FIG. 1, with the cassette 11 mounted in the illustrated position on the pump 10, the rounded end of the driver element 31 engages the membrane 73 distending it inwardly a slight amount through the opening 47 toward the cavity 40. The cassette is secured in this position with the cassette flush against the outer surface of the wall 16 by means of a pair of pivotal arms 77. The lower ends of the arms are provided with projections 79 which extend into guide slots 81 on opposite sides of the cassette 10 formed into the outer surface of the body member 39. Each of the slots 81 is provided with a shelf, not visible, against which the projections 79 abut.

The arms 77 provide means for retaining the cassette in place in operational relationship to the pump 10 and are also provided with means for releasing the cassette from the pump when the cassette is to be changed. To this end, each of the arms 77 is mounted on a pivot 83 and the ends of the arms 77 opposite the projections 79 are pivotally joined to a pair of links 85. The links 85 are pivotally mounted at the ends opposite the arms 77 to a cross bar 87 which, in turn, is mounted on a shaft 89. The shaft 89 is supported in a bearing 91 which may be molded integral with the wall 16. A coil spring 93 is wound about the shaft 89, having one end locked against rotary movement with respect to the bearing housing 91 and having the other end secured to the bar 87 at a position offset from the shaft 89. Accordingly, the spring 93 tends to hold the bar 87 in the illustrated position in FIG. 2. A lever 95 (shown only in FIG. 1) is provided attached to the shaft 89 and is manually operable to rotate the shaft 89 against the bias of the spring 93. By doing so, the linkage elements 85 cause the uppermost ends of the arms 77 to move toward each other, moving the projections 79 out of the slots 81 (shown partly in phantom in FIG. 2). This releases the cassette from the pump.

When the lever 95 is released, the arms 77 return to the position shown and a new cassette may be inserted. This is done by aligning the slots 81 with the projections 79 and pushing the cassette forward. The slots are so shaped as to cause the projections 79 to be forced outwardly on a ramp against the bias of the spring 93 until they clear the unillustrated shelves and snap back into the illustrated position to retain the cassette in place. Of course, other means of retaining the cassette in place may also be used within the scope of the invention.

For the purpose of effecting a positive ejection of the cassette when the manually movable lever 95 is actuated, a plunger 97 mounted on a rod 99 is provided. The rod 99 extends through an opening 101 in the wall 16 and is biased outwardly against a stop 103 by a coil spring 105 positioned in a recess 107 formed in the wall 16 and engaging the rod side of the plunger 97. When the cassette is urged into place, the plunger 97 is depressed into the recess 107 to allow the cassette to mate flush against the outer surface of the wall 16. Upon release of the projections 79 from the slots 81, the force of the spring 105 causes the cassette to move outwardly for easy removal.

The inner end of the rod 99 engages the actuating lever 109 of a switch 111. The switch 111 is suitably connected in the controlling circuitry to provide a safety interlock to prevent start of the pump unless the cassette is properly in place. The dimensions of the foregoing described elements are selected such that the membrane 73 is always distended slightly inwardly by the driver element 31 when the cassette is properly in position attached to the pump. As illustrated, the driver element 31 is in the position furthest to the left, that is, the outstroke position. When the driver element 31 is moved its maximum distance to the right, so that the left-hand one of the stop 29 engages the wall 15, the membrane 73 will be distended even further into the opening 47 than is illustrated. As a result, the driver element of the pump engages the membrane throughout movement of the driver element through its predetermined stroke distance. This ensures that the variation in volume during pumping operation is substantially constant despite variations in the size and relationship of the elements of the cassette and the pump due to variations within tolerances. It also ensures that no loss of contact occurs between the driver element and the diaphragm and also ensures that the diaphragm will pull back positively upon each stroke. Because the diameter of the driver element 31 is substantially smaller than the diameter of the opening 47, variations in alignment due to tolerance requirements are readily accommodated.

Preferably, the material of which the membrane or diaphragm 73 is constructed is a silicone rubber having a hardness of shore 70A± 5 points. For a membrane diameter of 0.860 inches and a thickness of 0.044 inches a preload of 0.030 inches, ±0.005 inches, has been found satisfactory. This using a diameter of the driver element of 0.312 inches with a 0.463 radius face and a stroke distance of 0.023 inches.

To purge the cassette, all that is necessary is to hold the cassette in an inverted position before attaching it to the pump. The fluid in the cavity 40 will flow out through the opening 43 and the nozzle 64, since the mushroom valve 69 is not retained in the opening.

During the operation of the previously described apparatus, the presence of air in the cavity 40 will not cause air to be pumped out of the cassette through the nipple 64. This is because the stroke distance or amount of compression of the cavity through movement of the membrane 43 is insufficient to pump air, but merely compresses the air present within the cavity. Thus, the device will not pump air into the patient.

The presence of air in the cavity 40, however, can result in a diminution of the pumping rate. Typically, a certain amount of air can be tolerated before this becomes of concern, usually about 10% fall off in pumping rate. Nevertheless, it is desirable to have some means for determining the presence of an excessive amount of air in the cavity 40.

To this end, the body member 39 is provided with the cap or bulb 49 at the top of the body member. The material of which this portion 49 is comprised is transparent. Any air present within the cavity 40 will rise to the bulb 49.

As may be seen in FIG. 2, when the cassette 11 is in position on the pump 10, the bulb 49 is positioned in the path of an optical sensor. The optical sensor includes an infrared emitter assembly 113 which may include a light emitting diode, and an infrared phototransistor detector assembly 117. The emitter assembly and detector assembly are mounted securely to the pump housing. When the cassette is loaded onto the pump, the presence of an air bubble in the bulb 49 will alter the refraction of the infrared light passing through the bulb 49. This decreases the intensity of radiation reaching the phototransistor, causing a voltage change. By suitably processing this voltage change in the electronic apparatus, by means not illustrated but well known to those skilled in the art, the pump may be shut off or suitable alarm may be activated. For example, the electronics may be designed to activate alarms or to switch the apparatus to a low flow rate when an air bubble of greater than 0.100 inch in diameter representing a 10% or more decrease in the flow rate is detected.

When initially inserting the cassette into the pump for operation, the cassette is primed. This is accomplished by turning the cassette upside down and filling the cassette with liquid through the nipple 53. This ensures that the cassette is completely full including the detector chamber 49.

Referring to FIG. 3, an intravenous delivery system employing a further embodiment of the present invention may be seen. The pumping system 20 and control electronics 21 are shown used in conjunction with an otherwise standard I. V. system. Thus a conventional bottle 22 with a drip chamber 24 may be attached to flexible hose 26, with the pumping system 20 being disposed between the tube section 26 and the remaining section of tube 28 coupled to the injection needle 30. Although bottle 22 is shown supported above the patient by some support structure 32, it can be placed in any suitable position without affecting system performance. Similarly, pumping system 20 is shown as supported at an elevated position by a support bracket 34, though it too may be placed in any suitable position. A pressure switch 23 clamped to a thin walled portion of hose 28 and an empty bottle detector 25 in hose section 26, are also provided, the details and function of which will be subsequently described.

Now referring to FIGS. 4 and 9, partial cross sections of the pumping system of FIG. 3 may be seen. The pumping system is comprised of two major portions, the cassette 36 which is disposable, and the pump 38 which provides a mechanical driving force for the pumping system in response to control electronics to be hereafter described.

The cassette 36 includes a body member 42 which preferably is an injection molded plastic member. The body member is formed to have an internal cavity 44, preferably rounded so as to be free of corners and to converge toward openings 45 and 46 at the top and bottom thereof. The lower portion of the body member has a downward extending cylindrical lip-like member 48 having a groove 50 therein to receive a mating protrusion on a semiflexible collector member 52 to retain and seal the collector member with respect thereto. The lower end of the collector member comprises a slightly tapered tube-like protrusion 54 for frictionally engaging the flexible tube 28 in a conventional manner.

Located within opening 46 and forming a unidirectional valve in cooperation therewith is a valve member 56 which may be spring loaded to the closed position by a leaf spring member 58. Details of a construction of this assembly are further illustrated in FIG. 9. The leaf spring member 58 normally encourages the valve member 56 to the upper or closed position by resting on the lower end 60 of the valve member. The leaf spring member 58 is a specially formed and shaped member of suitable material fastened to a pin 59 slideably fitting within a mating hole 61 in the lower portion of body member 42. When the pumping system is retained by the support bracket 34, an appropriately disposed portion of the bracket engages and deflects collector member 52 to force a pin 59 to its upper position, thereby moving valve member 56 to the closed position and preloading spring 58 by a predetermined amount. Proper orientation of the spring is assured throughout its movement by molded guides 62, as shown in FIG. 9.

At the top of the chamber is a valve comprised of a valve member 72 and a leaf spring 74, retained in position by an integrally molded plastic pin 76 passing through a cooperatively disposed hole, not shown, in lear spring 74 and attached thereto by a flared head, not shown. The preload on this valve, however, is preferably maintained at a minimum just adequate to hold the valve closed against the force of gravity, but inadequate to hold the valve closed against a force of more than a few inches of fluid pressure head. In this manner, relieving the preload on the lower valve will allow the fluid to flow from the container into the chamber against the upper valve, and similarly the air to flow out of the chamber to adequately prime the pumping system.

Now referring to FIG. 5, a further cross section of the pumping system 20 of FIG. 4 may be seen. The enclosure 44 within the body member 42 is defined in part by a flexible member 78, similar to a conventional bellows. The flexible member 78 is closed at the inner end 80, and is sealably retained in position with respect to body member 42 by a clamp plate 82, again maintained in position by formed pins 84. A drive rod 86 is coupled to the inner end of a flexible member 78 and is urged to an outward extended position by a compression spring 88.

The foregoing structure described in detail comprises what is referred to herein as the pump which may be coupled to a pump driver generally indicated by the numeral 90 in FIG. 5. For the purpose of coupling the cassette 36 to the pump 38, extending parallel members 94 are provided which snap over protrusions 96 on the body 42 (see also FIG. 10).

The pump 38 includes a solenoid actuator 98 having a movable actuator member 100 extending to abutting relationship with the drive rod 86 of the pump. The motion of the moving member of solenoid 98 is limited by two limit stop members 102, with a coil spring 104 urging the actuating member to its normally extended position. This position however, is specifically chosen in relation to the normal extended position of the drive rod 86 in the pump so that the actuator member 100 and drive rod 86 are normally encouraged to a tight abutting relationship by the coil spring 88. Accordingly, when the solenoid 98 is pulsed with an electrical signal on lines 106, the volume of chamber 44 is reduced by a small predetermined amount. This, in the normal operation, forces fluid out of the chamber 44 past the valve member 56 and outward through the collector 52 into the tube section 28. As a safety feature against the inadvertent pumping of air, the operating preload on spring 58 is such that unless chamber 44 is substantially full of fluid the air therein will merely compress upon the drive stroke of the pump without the lower valve opening. In this way, pumping of air is prevented, since the air is always located at the top of the chamber and the normal attitude of the valve is as shown.

Now referring to FIGS. 6 and 7, partial cross sections of another embodiment may be seen. This embodiment is similar in many respects to the previously described embodiment having a body member 110 with a top cap 112 cooperating to define an internal chamber 114. The top cap has an inlet valve member 116, lightly spring loaded to the closed position by the leaf spring 118. A lower valve member 120 is controlled by a leaf spring 122 fastened to a sliding pin 124, disposed just below the flexible collector member 126 (similar in function to the collector member 52 in the previous embodiment). Normally, with the pump removed from the driver as shown in FIG. 6, the pin 124 will slide to the outer or lower position as shown, thereby relieving the preload on valve member 120 and opening the lower valve for the bleeding of the system, and for allowing normal gravity feed infusion if desired, with the cassette detached from the pump. However, by pushing upward in the region generally indicated by numeral 126, the pin 124 may be forced to the upper position, thereby closing and sufficiently preloading the lower valve to avoid possible pumping of air and to permit controlled pumping of fluid with the pump as previously described.

One wall of chamber 114 is defined by a diaphragm, such as a plastic diaphragm 128, coupled to a drive rod 130. The diaphragm 128 may be a separately molded member cemented or welded in position in the body 110 or may merely be an integrally molded thin-walled section on the otherwise relatively thick and rigid body member 110.

As before, in the embodiment of FIG. 6, the lower valve is normally not preloaded with the cassette detached from the pump and therefore the cassette can be primed and the air very easily be bled from the system merely by the fluid pressure from an elevated fluid container. However, when the cassette is snapped into the pump, generally indicated by the numeral 140 in FIG. 7, a finger-like member 142 engages the collector member 126 just below the pin 124 and encourages the pin to the upper position to close and preload the lower valve. To assure proper orientation of the cassette with respect to the pump, the protruding section 144 on the cassette may be provided with a key 146 which must match a mating keyway in the mating member 148 on the pump with a detent such as a spring loaded ball 150 retaining the cassette with respect to the pump. Obviously other types of detent and/or retaining means may be used, such as by way of example, the well known bayonet connections or a connection similar to that shown with respect to the embodiments previously described. The pump 140 for this embodiment also contains a conventional solenoid, not shown in detail, driving an actuator member 152 and the drive rod 130 of the cassette. While not shown, if desired, a positive connection may be accomplished between drive rod 130 and actuating member 152 rather than the spring loading of these two members into abutment as shown.

Figure 13:
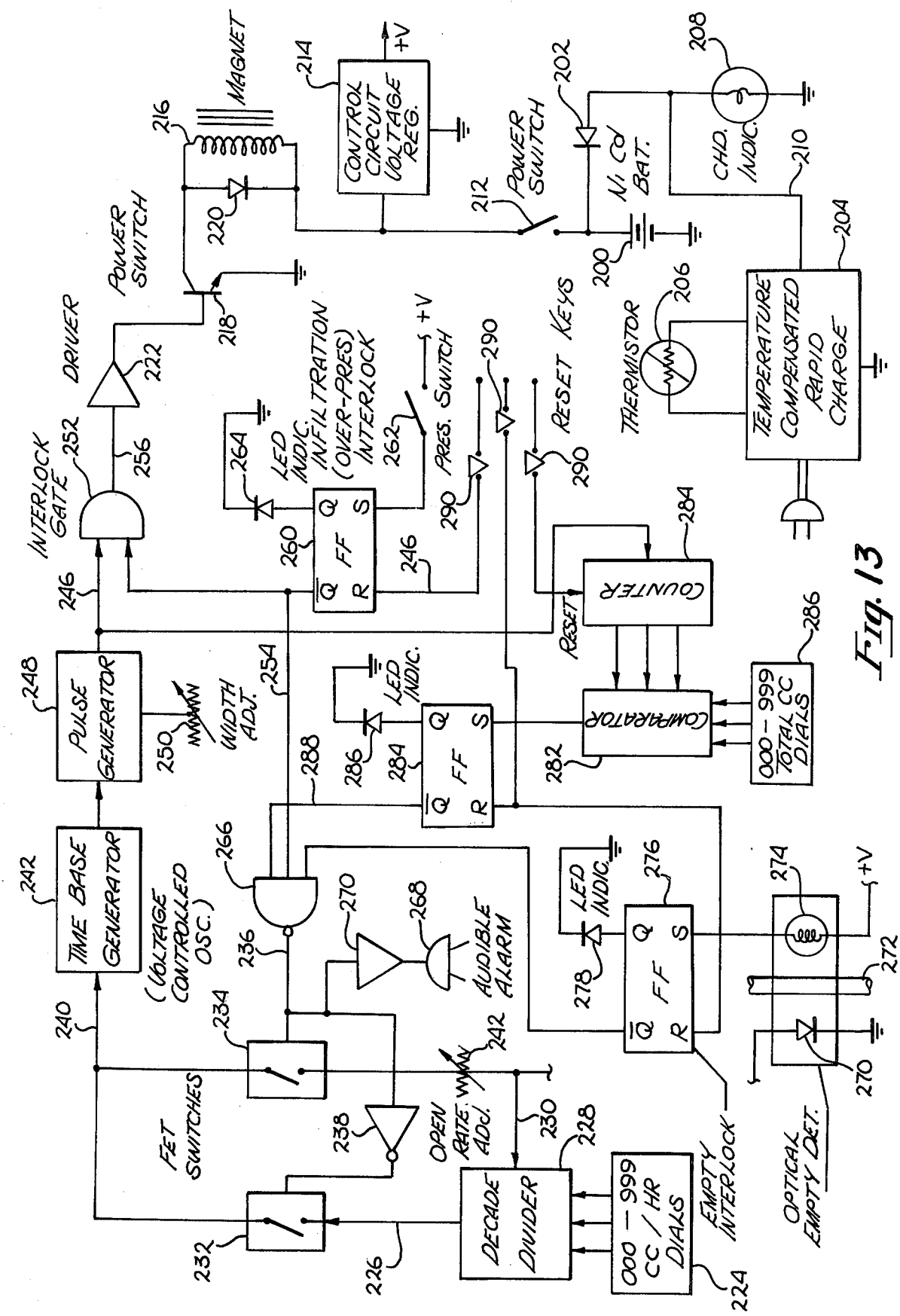
FIG. 13 is a schematic diagram of suitable control electronics.

Now referring to FIG. 13, a block diagram of suitable electronic circuitry for operating the invention may be seen. The power for the circuit is provided by a rechargeable nickel cadmium battery 200 which may be recharged through a diode 202 by recharger 204 of conventional design. Preferably, recharger 204 recharges the nickel cadmium battery at the maximum rate consistent with life and reliability considerations of the battery, and thus, thermistor 206 is utilized to sense the battery temperature and control the charger accordingly, with indicating light 208 indicating the proper operation thereof.

In the control electronics 21 a main ON/OFF power switch 212 provides power to a voltage regulator 214 for providing regulated voltage to certain elements in the remainder of the circuit, and also provides power to the solenoid 216, controllable through transistor switch 218. Thus, when the driver 222 provides current to the base of transistor 218, the transistor is turned on, thereby coupling the solenoid coil 216 across the battery. Diode 220 is provided as protection to transistor 218 when the transistor is turned off by providing for the orderly decay of the magnetic field in the solenoid.

Most of the remainder of the circuitry is comprised of CMOS logic circuits and field effect devices so as to require very little current, thereby allowing maximum duration of operation per battery recharge. The basic manual input for control of the infusion rate is provided by a three digit decade resistance coupled to the voltage reference to provide an analog signal on line 226 which is the analog of the dial reading on the dials of the decade resistance 224. A decade divider 228 provides a second signal on line 230 which is approximately one-tenth the signal appearing on line 226, with lines 226 and 230 being coupled to field effect transistors 232 and 234 respectively. These switches are controlled by a signal on line 236, switch 234 being directly controlled and switch 232 being controlled by the inverse of the signal on line 236 by inversion of the switching signal by inverter 238. Thus, either switch 232 or switch 234 is closed at any one time, but both switches cannot be simultaneously closed. Accordingly, the signals appearing on line 240 will be either the analog signal as commanded by the setting of the decade resistance 224, or will be on the order of one-tenth of that setting. To provide adjustment of the ratio between these two signals, a variable voltage divider 242 may be provided in the lower level signal path.

The analog signal on line 240 is applied to a time base generator 242 (a voltage control oscillator) so that the output frequency on line 244 is proportional to the analog signal on line 240, or more particularly, when switch 232 is closed, is proportional to the dial setting on decade resistance 224. The signal on line 244 is shaped to the desired pulse width on line 246 by a pulse generator 248, the pulse width being set by an appropriate adjustment 250. The requirement for the minimum pulse width is of course determined by the characteristics of the solenoid, and more importantly the dynamics of the pump when pumping fluid. An extremely short pulse will not result in any substantial pumping, whereas there is some pulse width beyond which increases in pulse width will not increase the pumping (per pulse or pump stroke). Thus, it is preferable to adjust the minimum pulse width to be approximately that pulse width above which no substantial increases in pumping will occur. The signal on line 246, depending upon the other input through gate 252 on line 254 is applied through line 256 to the driver 222 to drive the solenoid 216 through the power switch 218.

In the preceding description it was presumed that the gate 252 was ON and similarly the switch 232 was closed. Gate 252 is controlled by flip/flop 260 which is controlled by a pressure switch 262. The flip/flop is normally in the reset condition, giving a low state output as an input to light emitting diode 264 and a high state output on line 254 to enable the gate 252. The signal on line 254 is also applied as one input to the NAND gate 266. Upon the closure of the pressure switch 262, however, flip/flop 260 is set, changing the output to the diode 264 to the high state and the output on line 254 to the low state results in the signal on line 236 changing to the high state, turning on an audible alarm 268 through a driver 270. While the change in state on line 236 also turns off switch 232 and turns on switch 234 to drop the pulse rate by approximately one order of magnitude, this change has no affect since the pump has been completely disabled by gate 252.

The pressure switch 262 is shown in detail in FIGS. 11 and 12. The switch contains first and second body members 300 and 302. Preferably the injection molded body members are integrally connected by a hinge member 304 and retained in position by conventional lock 306. This assembly allows the opening of the two body members so that a length of flexible tubing 310 may be passed therebetween and the body snapped together as shown in FIG. 12. By selecting the length of tubing 310 to be relatively thin-walled tubing, such as the typically used thin-walled latex tubing section adjacent the needle, increases in fluid pressure therein will be transmitted through the wall of the tubing to a pressure plate 312 to communicate the pressure increase by way of mechanical motion to a micro-switch 314. A thumbscrew 316 is provided for the adjustment of the pressure switching level by adjusting the relative position of the switch with respect to the tube. Small changes in pressure may be sensed in this manner since the pressure plate 312 has a substantial area of contact with the tube 310 and small pressure changes result in substantial forces. Thus, if the infusion needle is misplaced such as being directed into soft tissue rather than into a vein, flow through the needle will be restricted and the pressure will rise above levels characteristic of proper intravenous infusion, thereby actuating switch 314 to shut off the system, light an indicator light to identify the cause of the shut-off, and sound an audible alarm so as to make the difficulty quickly known.

A second control which also may be used as a safeguard incorporates an optical sensor to sense the presence, or more appropriately the absence of the fluid being injected to control the system and also sound the alarm 268. For this purpoase a light emitting diode 270 may be disposed adjacent a fluid containing region, such as a transparent tube section 272, with a photo conducting light sensor 274 located opposite the light emitting diode and coupled to one input of a flip/flop 276. Obviously, for opaque fluids, presence of the fluid will block the light from the light emitting diode, thereby keeping the photo sensor 274 nonconducting. By proper selection of the optics, however, the defocusing effect of the presence of even a transparent fluid may be used to sufficiently limit the impingement of light on the sensor 274 so as to not set the flip/flop 276. Accordingly, when the section of tube between the diode and the photo sensor is exhausted, flip/flop 276 is set thereby turning on the light emitting diode 278 and driving line 280 to the low state, in turning driving line 236 to the high state through NAND gate 266 to turn on the audible alarm 268. This also opens switch 232 and closes switch 234 to greatly reduce the pumping rate.

A pressure switch similar to the one shown in FIGS. 11 and 12 could also be used to detect any empty bottle condition or absence of fluid. The switch would be placed between container 22 and pumping system 20 of FIG. 3. As the container empties, the pressure at the switch would decrease and at some preset value the switch would set fip/flop 276. The sequence of events after flip/flop 276 is set would be the same as those described in the preceding paragraph.

Another feature of the present invention is the capability to pump not only a widely variable, selected rate, but to pump a preset amount of fluid irrespective of excess amount of fluid in the container 22 (FIG. 3). For this purpose a comparator 282 is provided having a first input from counter 284 and a second input from a set of manually settable dials 286 (which in the preferred embodiment comprise three zero to nine digit dials, each providing an encoded input to the comparator 282). The counter receives an input on line 246 from the pulse generator 248, and once being reset counts the pulses, with the count of the counter constantly being compared with the preset count. Upon the coincidence of the count and the preset amount of dial 286, the output of the comparator will go to the high state, thereby setting flip/flop 284, turning on light emitting diode 286, and again dropping the signal on one input to the NAND gate 266 to again turn on the audible alarm. At the same time, switch 232 is opened and switch 234 is closed so that a low rate of delivery is maintained to prevent stagnation in the infusion set. The scaling so that the dials 286 correspond to a direct numerical reading of the total number of cubic centimeters delivered may be achieved by selecting the pump proportions and/or dividing down the pulse rate on line 246 before the direct count thereof.

In the previous description it was presumed that flip-flops 260, 284 and 276 and counter 284 were initially in the reset and zero count state. For this purpose purpose reset keys 290 are provided which each are coupled to the reset line of the flip/flops and counter so that momentary depression of a reset key 290 will set the respective system function to the prescribed initial state regardless of the previous occurrences.

Now referring to FIG. 8, an alternate form of outlet valve may be seen. In this embodiment, the spring 58a is located within a cast-in locating pocket on the bottom surface of the body member 42a and retained in position by an integrally molded plastic pin 64 passing through a cooperatively disposed hole in the spring. Preferably, the pin is flared to retain the spring in this desired position by ultrasonic or thermal forming techniques.

The opposite end 66 of the leaf spring is formed to the shape shown, with the lower portion 68 thereof being normally disposed just within the adjacent wall of the collector member 52. Located partly between the valve member 56 and the region 66 of the leaf spring 58 is a protrusion 70 on the lower surface of the body member 42, which in normal operation does not contact the spring, thereby allowing the spring to encourage the valve member 56 to the upward or valve closed position. However, when a force is applied to the end 68 of spring 58a by the manual deflection of the collector member 52, protrusion 70 becomes a fulcrum, causing the center portion of the spring to bow downward, thereby relieving the spring force on the valve member 56 and allowing the valve to open against the force of gravity to bleed the system. Thus, normally the preloaded leaf spring 58a is adequate to hold the valve closed even against a significant fluid pressure head (e.g. on the order of a few feet, as the source of the fluid to be injected will at most be only a few feet higher than the pump). However, for purposes of priming the pump, the spring may be deflected as shown so as to relieve the preload and to allow fluid and/or air to flow past the valve.

Now referring to FIGS. 14 and 15, an alternate embodiment for the pressure sensor of FIGS. 11 and 12 may be seen. This embodiment is similar to the previous embodiment but is a self-contained unit for coupling to an I.V. set with conventional couplings, with all parts in the pressure sensor which are exposed to the fluid being disposable. Thus, as may be seen in FIGS. 14 and 15, the body members 300a and 302a are somewhat elongated and are adapted to close about a flange 350 on hard plastic tube fittings 352 so as to present standard couplings to the I.V. hose sections 26. Between the two members 350 is coupled a flexible hose member 354, such as a thin-walled latex hose section, which is somewhat flattened by the pressure plate 312a. As before, a microswitch 314 is positioned against the pressure plate 312a by a thumbscrew adjustment 316. By having the hose section 354 flattened as illustrated in FIG. 14, pressure increases in the flexible section are transmitted to the pressure plate without requiring expansion of the hose section, e.g. the pressure increases tend to encourage the hose section to the round cross section, rather than requiring the expansion of an already round cross section of the embodiment of FIGS. 11 and 12.

In the embodiment described herein with respect to FIG. 3, the pressure sensor, the control electronics, the disposable cassette and detachable pump driver, and the fluid level sensor are all individual elements readily coupled together to form the complete system. However, it should be noted that the system may be fabricated as a self-contained system. Thus, while the various components which are exposed to the fluid stream will still be provided as disposable units, the control electronics 21 and pumping system 20 may be combined into a single unit for placement on a table beside the patient. Similarly, the bottle cotaining the fluid to be injected may be supported by the pumping system, as the system of the present invention does not depend upon gravity feed and therefore does not require that the bottle be substantially elevated. (While priming may require some elevation of the bottle with respect to the pump, a little excess length of hose between the container and the pump will allow temporary elevation of the container for priming). Inclusion of the battery charger into this one unit provides a complete self-contained I.V. system having all disposable parts in the fluid stream and otherwise incorporating all of the hereinbefore described features of the previous embodiments.

Now referring to FIG. 16, a schematic representation of an alternate embodiment using a stepper motor as the pump actuator may be seen. In this embodiment the drive pin 350 of the cassette 352 guided by sleeve bearing 351 is coupled to a connecting rod 356 by means of a tongue-and-groove joint 354. The connecting rod 356 is driven by an eccentric 358 on the shaft of stepper motor 360. With this arrangement the rotary action of the stepper motor 360 is converted to the required linear motion of diaphragm 362 of the cassette 352, providing positive drive during both the pumping stroke and the return stroke, and also providing accurate pumping rates by providing a short, but well defined stroke.

A stepper motor has the necessary response to function over a wide speed range, and unlike the solenoid does not require a return spring or stops to limit the diaphragm stroke. Other means of converting the rotary motion of the stepper to a reciprocating motion of the diaphragm, such as a crank-slider mechanism or a Scotch yoke, etc., may also be used.

There has been described herein a new and unique pumping system for use in an I.V. delivery system, together with apparatus for providing control signals to the controller for sensing misplacement of the needle, for providing both controlled delivery rates and controlled total delivery, and for sensing and shutting off the system upon misplacement of the needle. The system features a positive displacement disposable cassette which may be manufactured at low cost and shipped in sealed sterilized containers for one time use without any further required sterilization. The cassette is a simple molded cassette designed for quick assembly and easy attachment to a reusable pump, which in turn is operable from rechargeable battery operated control electronics.

While the present invention has been disclosed and described with respect to certain specific embodiments thereof, it will be understood by those skilled in the art that various changes in form and detail may be made therein without departing from the spirit and scope of the invention. Such modifications are intended to fall within the scope of the appended claims.

What is claimed is:

1. A system for pumping fluids for intravenous injection comprising a cassette, a pump and electric pump control means, said cassette having: a cassette body defining a chamber having an inlet port and an outlet port, said inlet port having a means for coupling to a source of fluid to be injected; first valve means coupled to said inlet port for allowing unidirectional flow into said chamber through said inlet port; first valve biasing means for preloading said first valve means to a closed position an amount so as to be opened by a substantial fluid pressure above said first valve means, second valve means coupled to said outlet port for allowing unidirectional flow out of said chamber through said outlet port; second valve biasing means for preloading said second valve means to a closed position an amount so as to be opened by a substantial fluid pressure in said chamber, said second valve biasing means including means for relieving the bias of said second valve means to the closed position when said cassette is decoupled from said pump; movable means comprising a diaphragm defining a part of said chamber for varying the volume of said chamber in response to movement of said movable means, and collector means coupled to said outlet port for directing fluid from said outlet port toward a needle; said pump having: means for detachably coupling to said cassette; a linear actuator movable between first and second positions by an electrical signal for providing a mechanical motion in response to electrical input, said actuator being engageable with said diaphragm on said cassette when said pump is coupled to said cassette and being positioned such that said diaphragm is always distended inwardly by said actuator throughout movement thereof between said first and second positions, said electric pump control means being means for providing a periodic electrical signal to said pump, said control means further having means for controllably varying the period of said electrical signal.

2. The system of claim 1 wherein said actuator means include a stepper motor.

3. The system of claim 1 wherein said electric pump control means are adapted to periodically provide an electrical pulse to said actuator means.

4. The system of claim 1 wherein said electric pump control means are adapted to operate on a battery power supply.

5. The system of claim 1 wherein said cassette body includes an opening therein, and wherein said movable means comprise a diaphragm extending across said opening to form part of the confines of said chamber.

6. The system of claim 1 wherein said electric pump control means include means for providing a repetitive signal to said actuator means, and means for manually setting the frequency of repetition of said repetitive signal.

7. The system of claim 6 wherein said electric pump control means further include means for altering said repetitive signal upon the occurrence of a predetermined number of repetitions of said repetitive signal.

8. The system of claim 7 comprising means for manually setting said predetermined number.

9. The system of claim 1 further including pressure sensor means for terminating said periodic electrical signal upon increases in pressure in the outlet of said pump.

10. A cassette for a pump having an activating projection thereon, said cassette comprising: a cassette body with a chamber having an inlet port and an outlet port, said inlet port having means for coupling to a source of fluid to be injected; first valve means coupled to said inlet port for allowing unidirectional flow into said chamber through said inlet port; second valve means coupled to said outlet port for allowing unidirectional flow out of said chamber through said outlet port, said second valve means having biasing means for controllably preloading and unpreloading said second valve means; said second valve biasing means preloading said second valve means to a closed position an amount so as to be opened by a substantial fluid pressure in said chamber; said second valve biasing means having a portion thereof engageable by the actuating projection on the pump to render said second valve biasing means operable, a diaphragm defining a part of said chamber for varying the volume of said chamber in response to movement of said diaphragm; collector means coupled to said outlet port for directing fluid from said outlet port toward a needle; and means for coupling said diaphragm to an actuator.

11. A pumping system for use in an intravenous delivery system, comprising, a pump including a driver element adapted for reciprocatory motion through a predetermined stroke distance upon energization of said pump, and a disposable cassette adapted to be detachably secured to said pump, said cassette having wall means defining a chamber with inlet and outlet ports adapted for series connection in the flow of fluid in the intravenous delivery system, said wall means including a deformable portion for varying the volume of said chamber, said driver element of said pump being positioned to engage said deformable portion of said wall means with said cassette secured to said pump throughout movement of said driver element through predetermined stroke distance, preloaded valve means in said outlet port providing a unidirectional flow of fluid therethrough out of said chamber, wherein projecting means are provided on said pump for engaging said valve means in said outlet port with said cassette secured to said pump to maintain the preloading of said valve means in said outlet port, said projecting means being disengageable from said valve means when said cassette is detached from said pump, whereby said valve means in said outlet port are no longer preloaded.

* * * * *